(12) United States Patent
Williamson et al.

(10) Patent No.: US 10,940,093 B2
(45) Date of Patent: Mar. 9, 2021

(54) APPARATUS AND METHOD FOR DISPENSING PHARMACEUTICALS AND OTHER MEDICATIONS

(71) Applicants: John R. Williamson, Bloomington, MN (US); David R. Williamson, Climax, MI (US)

(72) Inventors: John R. Williamson, Bloomington, MN (US); David R. Williamson, Climax, MI (US)

( * ) Notice: Subject to any disclaimer, the term of this patent is extended or adjusted under 35 U.S.C. 154(b) by 0 days.

(21) Appl. No.: 15/492,627

(22) Filed: Apr. 20, 2017

(65) Prior Publication Data

US 2017/0304153 A1  Oct. 26, 2017

Related U.S. Application Data

(60) Provisional application No. 62/325,129, filed on Apr. 20, 2016.

(51) Int. Cl.
*A61J 7/04* (2006.01)
*A61J 7/00* (2006.01)
*G06F 17/00* (2019.01)
*G07F 17/00* (2006.01)
*G07F 11/44* (2006.01)
*G16H 20/13* (2018.01)

(52) U.S. Cl.
CPC ........... *A61J 7/0084* (2013.01); *A61J 7/0427* (2015.05); *G07F 11/44* (2013.01); *G07F 17/0092* (2013.01); *G16H 20/13* (2018.01); *A61J 7/0418* (2015.05); *A61J 2200/30* (2013.01); *A61J 2200/74* (2013.01)

(58) Field of Classification Search
CPC ..... G07F 17/0092; G07F 11/44; A61J 7/0427; A61J 7/0084; A61J 7/0418; A61J 2200/30; A61J 2200/74; G16H 20/13
USPC .................................................. 700/231–244
See application file for complete search history.

(56) References Cited

U.S. PATENT DOCUMENTS

| | | | | |
|---|---|---|---|---|
| 4,763,810 A | * | 8/1988 | Christiansen | A61J 7/04 221/15 |
| 5,097,982 A | * | 3/1992 | Kedem | A61J 7/0084 221/3 |
| 5,768,327 A | * | 6/1998 | Pinto | G01V 8/20 377/10 |
| 5,907,493 A | * | 5/1999 | Boyer | G06F 19/3462 700/231 |
| 7,048,141 B2 | * | 5/2006 | Abdulhay | G07F 11/10 221/15 |
| 7,213,721 B2 | * | 5/2007 | Abdulhay | G07F 11/10 221/124 |
| 7,263,411 B2 | * | 8/2007 | Shows | G06F 19/3462 221/2 |

(Continued)

*Primary Examiner* — Michael Collins
(74) *Attorney, Agent, or Firm* — Billion & Armitage

(57) ABSTRACT

A medication dispensing apparatus includes a housing for at storing at least one medication in bulk, a dispenser and a verification sensor. The at least one medication including a plurality of doses of the at least one medication. The dispenser separates a single dose from the at least one medication in bulk. The dispenser moves the single dose of the at least one medication from a position within the housing to a position outside the housing. The verification sensor verifies that the at least one medication is a correct medication.

24 Claims, 9 Drawing Sheets

(56) References Cited

U.S. PATENT DOCUMENTS

| | | | | |
|---|---|---|---|---|
| 7,711,449 B2* | 5/2010 | Abdulhay | ............... | G07F 11/10 221/13 |
| 8,009,040 B2* | 8/2011 | Kennedy | ............. | G06F 19/3462 340/540 |
| 8,108,068 B1* | 1/2012 | Boucher | ............... | A61J 7/0084 700/236 |
| 8,271,128 B1* | 9/2012 | Schultz | .................... | A61J 7/02 700/236 |
| 8,483,872 B2* | 7/2013 | Ratnakar | ............... | A61J 7/0445 700/240 |
| 8,855,811 B1* | 10/2014 | Schultz | .................... | A61J 7/02 700/236 |
| 9,043,015 B2* | 5/2015 | Ratnakar | .................... | A61J 7/02 700/241 |
| 9,501,626 B2* | 11/2016 | Zhang | ................. | G07F 17/0092 |
| 2004/0034447 A1* | 2/2004 | Vollm | .................... | B65B 5/103 700/235 |
| 2006/0201961 A1* | 9/2006 | Abdulhay | ............... | G07F 11/10 221/9 |
| 2008/0195249 A1* | 8/2008 | Rousso | .................. | A61B 5/417 700/231 |
| 2010/0268380 A1* | 10/2010 | Waugh | .................... | G07F 11/44 700/239 |
| 2012/0004770 A1* | 1/2012 | Ooyen | ................ | G06F 19/3462 700/235 |
| 2014/0358278 A1* | 12/2014 | Zhang | ................ | G07F 17/0092 700/240 |
| 2015/0227127 A1* | 8/2015 | Miller | .................. | G10K 11/178 700/244 |

\* cited by examiner

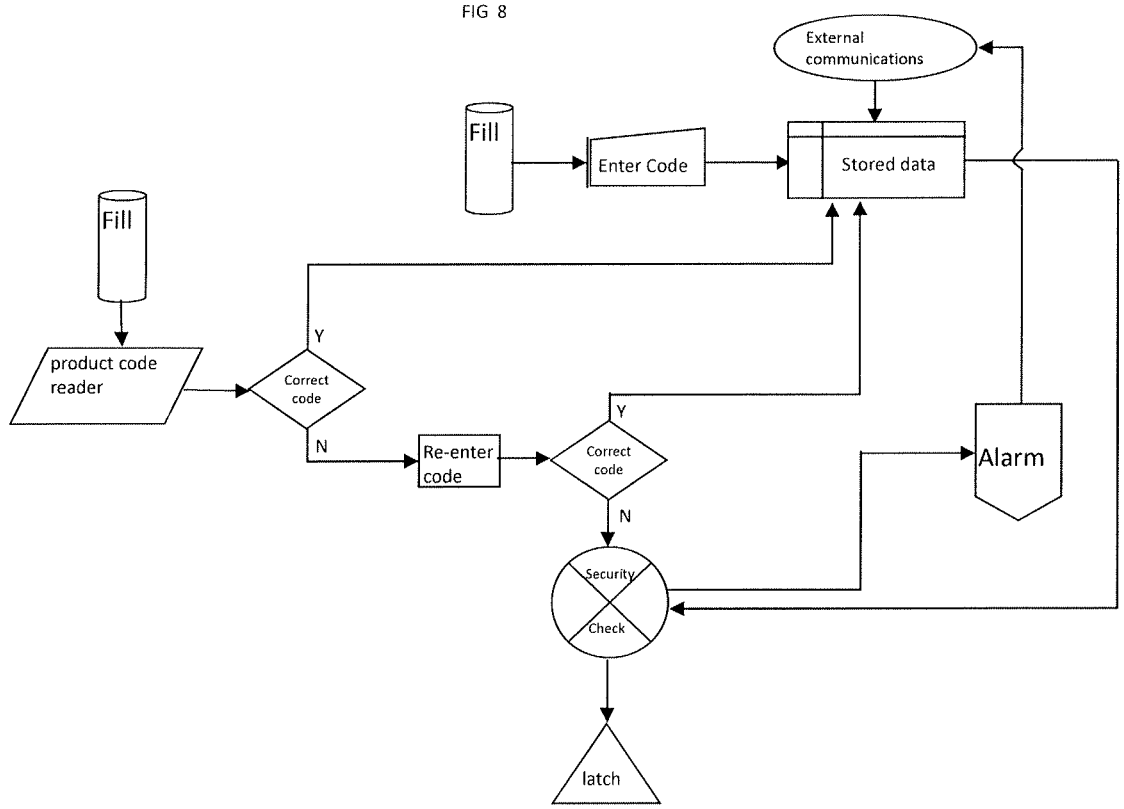
FIG 8
Storage confirmation
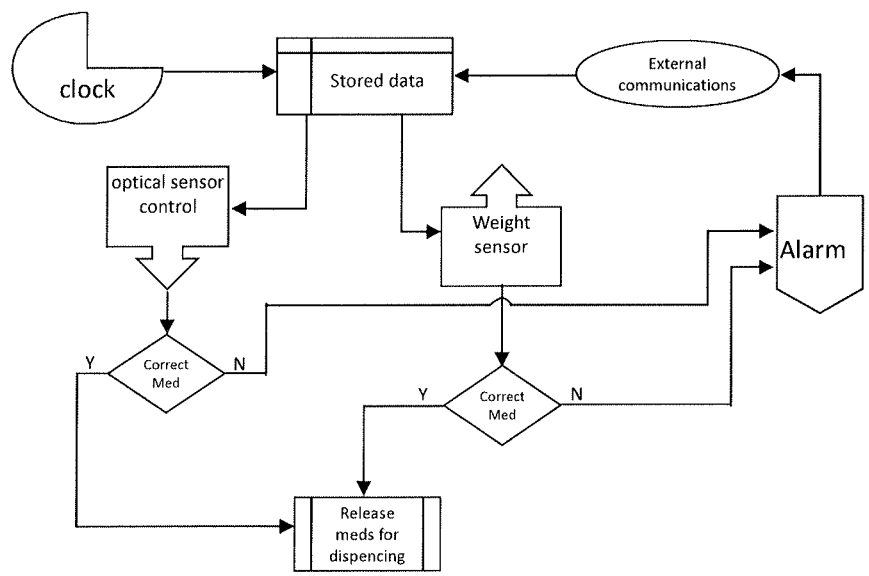

Dispensery stage 1 single sort
FIG 9
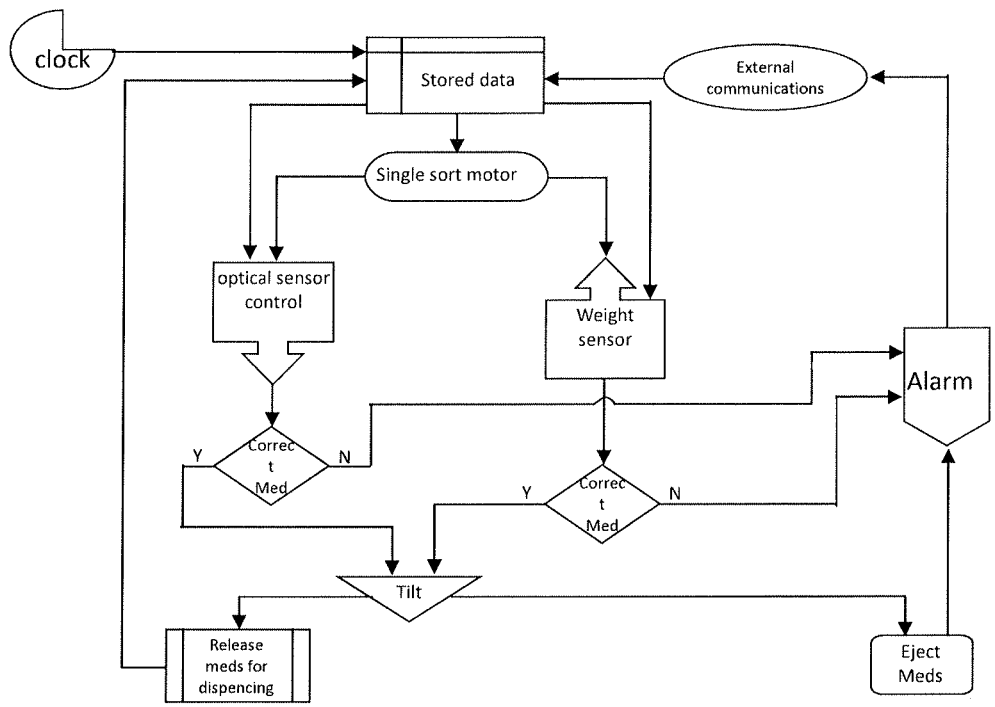
Despensery stage 2
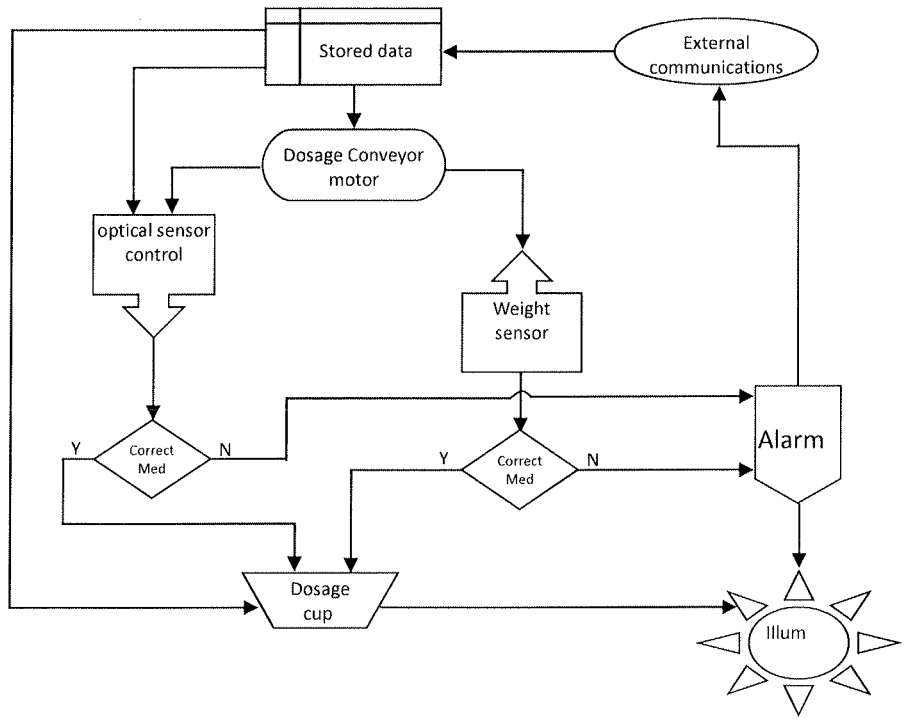

APPARATUS AND METHOD FOR DISPENSING PHARMACEUTICALS AND OTHER MEDICATIONS

FIELD OF THE INVENTION

The present invention relates to an apparatus and method for dispensing pharmaceuticals and other medications. More specifically the invention secures the medications, monitors the patient and prompts the patient to comply with the prescription. The device also verifies the prescription.

BACKGROUND

It is common that the individuals are prescribed or choose linctus medications and/or supplements for regular consumption. The complications with this linctus consumption includes remembering to take the medication, tedious sorting individual dosages, following proper prescribed consumption procedures, maintaining stock of linctus products and security of stored linctus against misuse. Certain third parties such family members, nursing care givers, prescribers, pharmacists, Non-Government and Government entities and product manufactures have indicated concerns that some linctus medications and/or supplements can be misused either by inadequate attention to the directions for consumption, not remembering to take the prescribed dosage, over mediating and other errant or abusive behaviors.

Keeping medications secure can prevent or curb drug abuse. Certain prescribed medications are commonly stolen by people visiting a home. Many times, the patient is prescribed a pain killer, or a narcotic and sent home from a hospital. The patient takes the medication as needed. Many times the patient will stop taking such medications as soon as possible and leave the prescription in the medicine cabinet as the patient may feel they may need it again. In other instances, the patient may even forget he has the medication in the cabinet. Some people visiting homes, intentionally rifle through medicine cabinets or other areas where these medications are stored. These characters generally sell the ill-gotten prescribed medicines to others who abuse the medications. In short, security for these types of medications is a big concern.

Compliance or getting patients to take their prescriptions is another concern. People may be prescribed to take an entire course of antibiotics. Others are placed on daily medications. In many instances, when the patient feels better, the patient will stop taking the medications. Many times to their detriment. For example, when a patient stops in the middle of the course of antibiotics rather than completing it, the patient risks getting sick again or risks not completely knocking out the bacteria that caused the problem. Some patients take daily medications to control depression or other mental disorders. If they stop the medications, depression and other harmful behavior may ensue. This is a problem. Some health insurance companies or federal programs have used compliance as a metric to measure the effectiveness of health care delivery. So any device or method that can increase compliance is looked upon favorably by the medical community.

SUMMARY OF THE INVENTION

This invention is a method and apparatus that provides a monitored and secured consumer assured pill, caplet, tablet, or the like. The invention is a linctus dispensary and management process. This present invention includes multiple levels of verification of the dosage being dispensed. The present invention communicates all apparatus real-time and historical operating functions to remote monitoring of service providers consisting of variety entities.

Certain consumers find the process of sorting the week dosage a time consuming tedious arduous chore. The present invention provides the convenience of a single sort. The sort occurs in this invention at the initial, monthly or quarterly storage cylinder section fill. Time is the basis digital function of the processors calculated with adjustability to morning, hourly, daily and monthly dosage. Security measures included to limit access to the stored prescriptions. Dispensing of the linctus is facilitated by an acknowledgement process inputted by the consumer. This input is only authorized at the appropriate time per the prescriber's directions.

This present invention offers the consumer a simplified and convenient means to receive, store, dispense, and manage the pills and tablets for medications and/or supplements they consume regularly. The local processors and sub processors in this invention gather, retain, and verify specific product data. The data includes the physical characteristics used by the present invention to facilitate the storage, dispensing and consumption notification of linctus products with in the device. These onboard processors provide consumers and or interested third parties with monitored and secure assured administration of proper dosage of tablet and/or pill medications and/or supplements, at the appropriate intervals with the appropriate directions for consumption displayed on the unit mounted display. This invention provides the user dispensing without the need to sort the linctus products into daily, weekly or monthly containers. The device provides various levels of notifications and alarms to the consumer of the need to consume the medications and/or supplements and conditions of stored products, device status and history. The device annunciates these alarm functions with an audible sound, visual display and digital communications. This invention communicates the device data relative to the storage, linctus processes of conveyance, sorting, dispensing and consumption of the linctus products. Data and alarms obtained and processed by the device logic components maybe transmitted via a virtual private network to parties of interest. The consumer is automatically provided the proper sorting by passing the retail prescription container pass the retail container scanner. The scanner provides data input into this inventions program that includes specific prescription information. The specific information may be also provided with radio, barcode, or other product identification markers. The identification data may also include the specifics of the directions to consume the prescriptions.

BRIEF DESCRIPTION OF THE DRAWINGS

The invention is pointed out with particularity in the appended claims. However, a more complete understanding of the present invention may be derived by referring to the detailed description when considered in connection with the figures, wherein like reference numbers refer to similar items throughout the figures and.

FIG. 8 is a logic diagram for operation of certain aspects of the present invention apparatus, according to an example embodiment.

FIG. 9 is a logic diagram for operation of certain aspects of the present invention apparatus, according to an example embodiment.

The description set out herein illustrates the various embodiments of the invention and such description is not intended to be construed as limiting in any manner.

DETAILED DESCRIPTION

Figure 1:
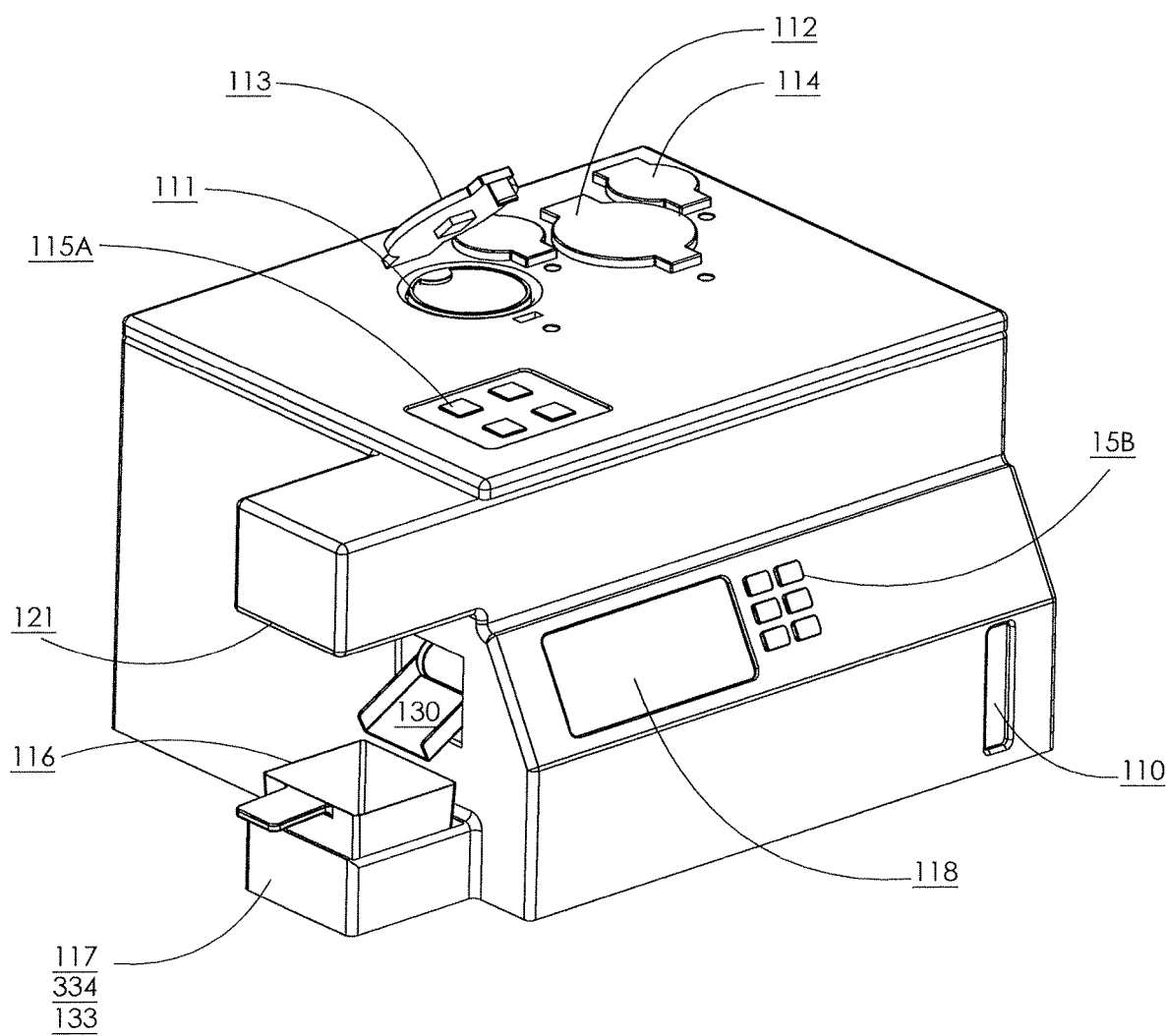
FIG. 1 is a perspective view of the medication dispensing device, according to an example embodiment.

FIG. 1 is a perspective view of the medication dispensing apparatus 100, according to an example embodiment. The medication dispensing apparatus 100 includes a housing 102. Mechanical devices and electrical devices are positioned within the housing 100 to control and monitor the dispensing of the pharmaceutical and linctus products dispensed by the dispensing apparatus 100. Visible on the exterior of the housing 102 is a digital reader 110 which obtains coded information from the linctus product label or pharmaceutical bottle label (shown in FIG. 5). The digital reader 110 can be any type of reader, including a bar code scanner or a QR scanner or the like. The medication dispensing apparatus 100 includes a plurality of storage cylinders or storage containers, such as 111. The containers each include a lid, such as lid 113 for container 111. Lid 113 is shown in an open position. The other containers (not shown) have lids 112, 114 in a closed position. The lids 112, 113, 114 of the storage containers or storage cylinders close securely to prevent others from tampering or stealing prescription medications or linctus placed within the storage containers or cylinders. Three lids depicting three storage cylinders or containers are shown in FIG. 1. It should be understood that the medication dispensing apparatus 100 can have many more containers or even less than three containers for holding medications or vitamins to be dispensed. It should also be understood that the lids 112, 113, 114 can be locked securely and can be programmed to stay locked until a refill of the prescription stored therein is received and the label read for the refill. The medicinal dispenser, in some embodiments, stores the location of certain prescriptions and opens the appropriate lid 112, 113, 114 for the medication therein. Keeping the lids 112, 113, 114 locked also enhances security. The housing 102 also includes a dispensary cup receiver base 117. A removable dosage dispensary cup 116 fits within the dispensary cup receiver base 117. A digital graphic display 118 is also positioned on the exterior of the housing 102. A series of buttons depicted at locations 115A and 115B are part of an operator command interface. The digital graphic display 118 can be any type of screen. The digital graphic display 118 can display prompts for the user. In another embodiment, the digital graphic display 118 can also be a touch panel. The display can display prompts for user input. The user can answer the prompt using buttons 115A, 115B, 115C, 115D to produce a signal denoting a response to the prompt. In the other embodiment, the touch screen can be touched to answer prompts and generate a signal. The dispensary cup receiver base includes an alarm illumination device 334. The alarm illuminates the receiver cup 116 when there is a medication or there are medications to take. Also on the exterior of the housing 110 is a chute 130. Medications are selected and sorted inside the medication dispensing apparatus 100 and placed at the chute 130 for dispensing into the receiver cup 116. The alarm can also be audible in some embodiments. The illumination ceases when the medications have been removed. The patient is then thought to have taken their medications. This is a way to help with compliance with respect to patients taking their prescribed medications and linctus. The dispensary cup receiver base 116 also includes a scale or cup weight sensor. The weight of the dispensed medications can be measured as a further verification that the medication dispensed is correct. For example if a combination of three pills came from three compartments, the weight of the combination is known. By subtracting the weight of the dispensary receiver cup 116 from the weight of the receiver cup 116 and the pills the weight of the pills is known. The combined weight of the pills should be substantially equal to the summed weight of all the pills. Above the dispensary cup is another sensor 21 (shown in FIG. 3 and discussed below) In another embodiment, the receiver cup 116 and the receiver base 117 could be kept in a lockable portion of the housing 102. This would be done to make the system more secure. The patient would have to verify identity before the portion of the housing 102 would be unlocked to allow access to the receiver cup 116 and the receiver base 117. This would enhance security in the event the patient was taking narcotics or pain killers or other drugs which might be more likely to be abused by others.

The housing 100 and other components can be made of any appropriate material, such as wood metal or a polymer based material or the like. The housing material provides support, an enclosure and some ascetic value. The display 118 can be a digital interface to the device 100. A person, such as a patient, can program the initial operational data to display information on the processes and linctus products processed by the present invention. The displayed information can include, but is not limited to, time, AM, PM, special instructions for consumption such as Take with meal or Take with milk, return container, refill required, errant or proper operation activities and the like. The present invention resolves the complication of remembering to take the med at the prescribed dosages and time by way of an alarm. The device alarm functions can include a lighted display and an audio function.

Certain consumers depend on an alarming device to mark the time for consumption of the medications and supplements. The present invention is intended for home use by persons may be prescribed regular medications and/or supplements. Remote or away consumption may also be facilitated through external communications of the device. The device dispenses the proper dosage at the prescribed time. The device monitors the linctus throughout the processes involved dispensing for accuracy.

The housing mounted digital output data display 118 can notify the consumer that a specific scheduled prescription must be consumed. The display 118 will include directions for the particular consumer at the appropriate time. These instructions to the consumer will tell the consumer to remove the medication or medications from the dispensing container. The dispensing container is the receiver cup 116 that holds the prescriptions distributed from the device. The consumers may also be directed take the medications with a meal or with a full glass of water in compliance with the prescription, for example. The digital display 118 can also include information to direct the consumer to refill the storage container with a prescription refill. The display 118 can also prompt the user to request a refill. In some embodiments, the machine 100 can request the refill.

Figure 2:
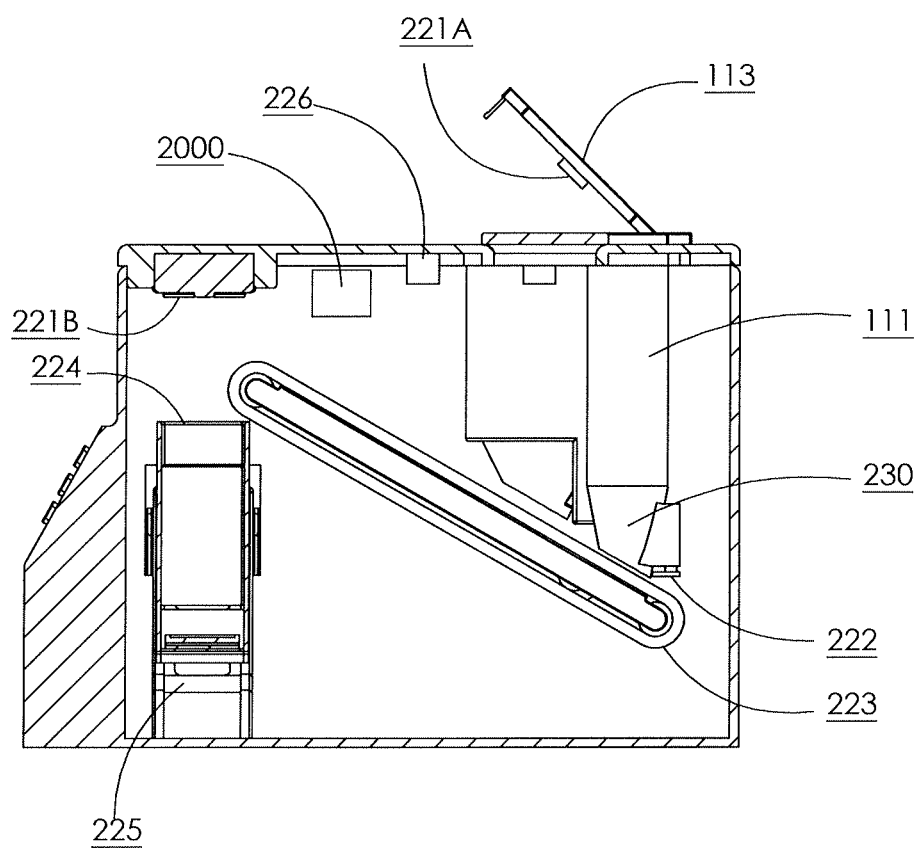
FIG. 2 is a cross sectional view along line 2-2 in FIG. 1 that shows the locations of the internal components that store, sort and verify the individual linctus products, according to an example embodiment.

FIG. 2 is a cross sectional view along line 2-2 in FIG. 1 that shows several internal components that store, sort and verify the individual linctus products, according to an example embodiment. The internal components include the product storage cylinder or storage container 111. The internal components include a weight sensor 222, an optical lid sensor 221A, an optical conveyor sensor 221B, an electromechanical locking mechanism 226, a sorting separator belt 223, a dosage hopper 224 and a dosage conveyor 225. The product storage cylinder or storage container 111 rests on the weight sensor 222. The storage cylinder secure lid 113 carries the lid sensor 221A. The electromechanical locking mechanism 226 is shown in an open position. The electromechanical locking mechanism or electric magnet includes a catch which engages a portion of the lid 113 to lock it in the closed position. The electromechanical locking mechanism 226 can include a solenoid and a spring plunger or electric magnetic. The catch is attached to the spring plunger. When the solenoid is energized if produces a magnetic force which pulls the plunger into the solenoid and disengages the catch from the lid 113 of the storage container 111. The de-energized position is with the catch engaging the lid 113 in the closed position. Once locked, the container 111 is not accessible to people other than those that might know a password that must be entered at the interface, such as at buttons 115A, 115B or the screen 118 (See FIG. 1). The interface 115A, 115B or 118 can include a print detector capable of matching a finger or thumbprint of the patient to one in memory to verify the identity of the user. In some embodiments, an interface could also include a device for reading the retina of a user to verify identity. In another embodiment, the latching mechanism 226 prevents access to the storage container 111. A security function is initiated at the time of filling wherein the container lid 113 latch 226 is released to allow the container to be opened and filled. Once filled the lid 113 is closed and sealed until the next fill process.

The weight sensor 222 senses the weight and optical sensors 224 detect physical characteristics and data of an individual medication and verifies a proper dose. Once verified by the weight sensor 222 and optical sensor 224, the medication is placed on the sorting separator belt 223. The sorting separator belt 223 leads from the storage cylinder 111 to the dosage hopper 224. Positioned near one end of the dosage hopper 224 is the optical sensor array 221B. The optical conveyor sensor or sensor array 221B checks the medication for size and color. Weight sensor 332 mounted with in the tilting dosage verification platform 331 verifies the sorted medication weight. It also verifies once more that the dosage is correct. Errant medication is rejected. Properly verified linctus are processed to the dosage conveyor 225. This is still further verification that the correct medication is being dispensed. Below the dosage hopper 224 is the dosage conveyor 225. The dosage conveyor 225 moves the verified medication to the chute where the medication is placed on the chute 230 and dispensed into the dispensing cup 116. The medication dispensing apparatus 100 can include a computing device 2000 which will be described in further detail in FIG. 5.

Figure 3:
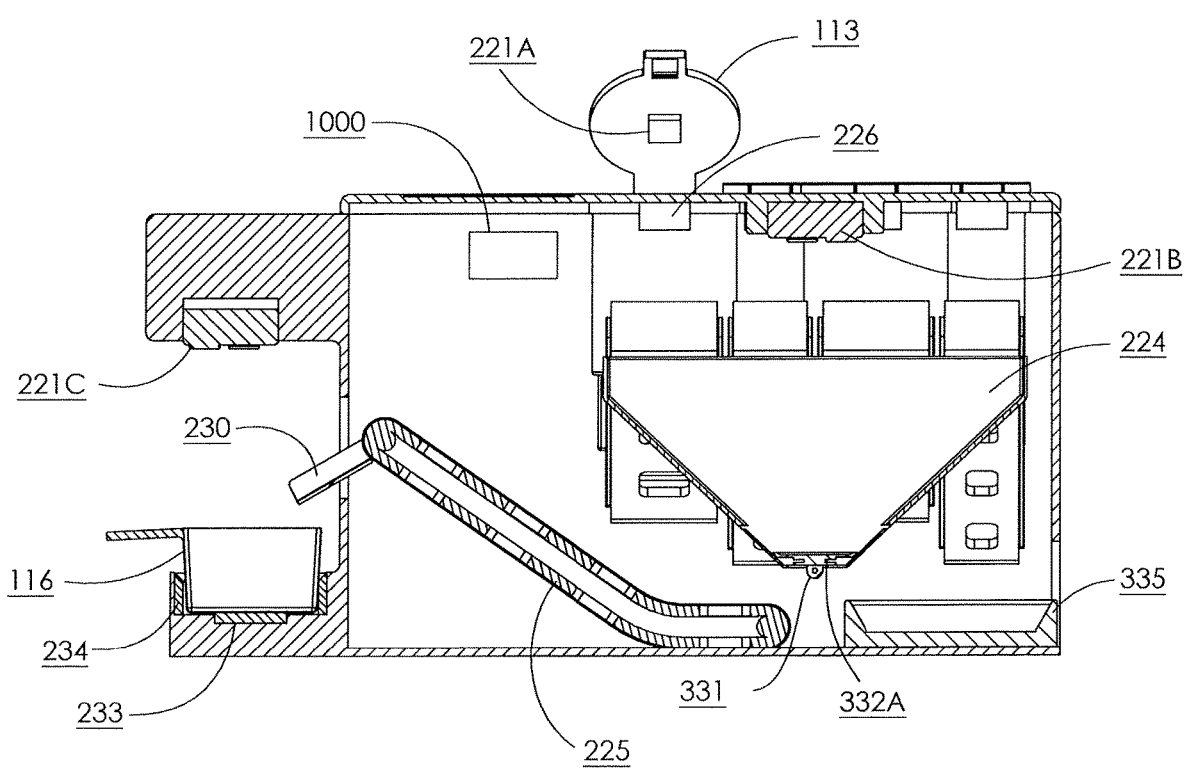
FIG. 3 is a longitudinal sectional view along line 3-3 in FIG. 1 that shows the configuration of the storage cylinders, the secure storage cylinder lid with the optical sensor mounted on the interior of the cylinder lid, according to an example embodiment.

FIG. 3 is a longitudinal sectional view along line 3-3 in FIG. 1 that further details the configuration of the storage cylinders, such as 111, the secure storage cylinder lid 113, 112, 118 with the optical sensor 221A mounted on the interior of the cylinder lid 113, according to an example embodiment. FIG. 3 also shows the storage lid latching mechanism 226. The medication dispensing apparatus 100 also includes a single dosage sorting separator 230 in conjunction belt 223 utilizing escapement process which is a calibrated opening belt that is moved past the bottom opening of the storage container 111) and The single unit is moved on belt 223 to the top opening of hopper 224 and verified by hopper optical sensors 221B mounted above the hopper 224. At the bottom of the hopper 224 is a single dosage verification platform 332. The single dosage verification platform 332 is further described with respect to FIG. 4. The dosage verification platform 332 serves as a floor for the hopper 224. The floor stays level while the optical sensor 221B takes an image of the medication and compares the medication in the hopper 224 and specifically on the floor of the pivoting dosage verification platform 332. It the medication is determined to be correct, the dosage verification platform 332 tilts toward the sorting separator belt 223 which in turn leads to the dosage conveyor 225 and to the chute 224. If the dosage or medication is determined to be incorrect, the dosage verification platform 332 tilts toward an errant dosage receptacle 335 and the incorrect medication is placed into the errant dosage receptacle 335. Both the errant dosage receptacle 335 and the end of the sorting separator belt 223 are below the hopper 224. The correct and verified medications are placed on the dosage conveyor 225 which coveys the medication to the chute 230. The medication, as verified, travels down the chute 230 and to the dosage dispensary cup 212. The dispensary cup receiver base 116 includes the weight verification platform 133 and dispensary alarm illumination source 134 that illuminates the cup 112. Mounted above the dispensary cup 112 is yet another optical verification sensor 221C. The computing device 1000 is also shown in FIG. 3. The computing device can be a programmable logic controller, microprocessor, a plurality of microprocessors, or the like. The computing device 1000 is shown schematically is a box and will be further described below.

Figure 4:
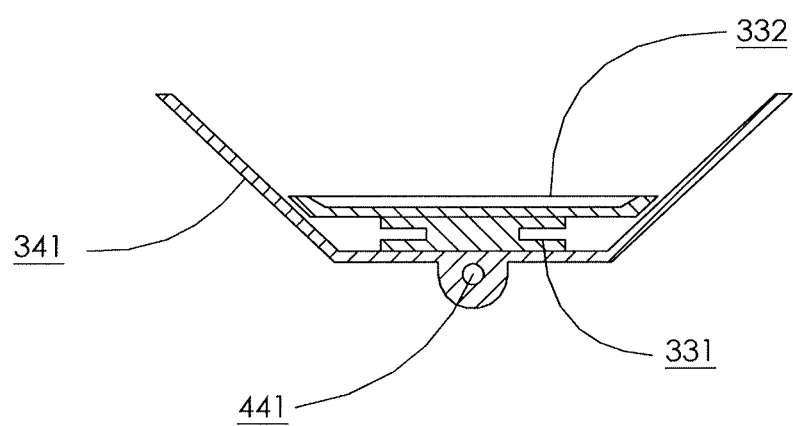
FIG. 4 shows in detail the dosage verification pivoting platform with the weight sensor, according to an example embodiment.

FIG. 4 shows in detail the pivoting platform 341 that includes a floor 332 of the pivoting platform and a weight sensor 331, according to an example embodiment. The pivoting platform 341 is shaped to correspond to the bottom portion of the hopper 224 (shown in FIG. 3). The pivoting platform 341 pivots about pivot axis 441. The pivoting platform 341 is mounted to a shaft (not shown). The longitudinal axis of the shaft is substantially the same as the pivot axis 441. The floor 332 of the pivoting platform 341 includes the weight sensor 331. The weight sensor 331 provides for added verification. The medication has a weight. The medication is weighed as one aspect of verification. If within the proper range, the medication is not eliminated as improper. As noted above, there is also a sensor 221B above the platform 341. The sensor 221B is an optical sensor. The medication is viewed to determine a color, shape, imprinted characteristics and size. The sensor 221B is used to further verify the medication. If the medication in the hopper and on the pivoting platform is determined to be correct and correspond to a medication the patient is supposed to be taking, the platform is pivoted counterclockwise or toward the conveyor 225 which takes the medication to the delivery chute 230. If the medication is improper or incorrect, the platform is pivoted in the clockwise direction and the medication is placed in the errant dosage receptacle 335.

Figure 5:
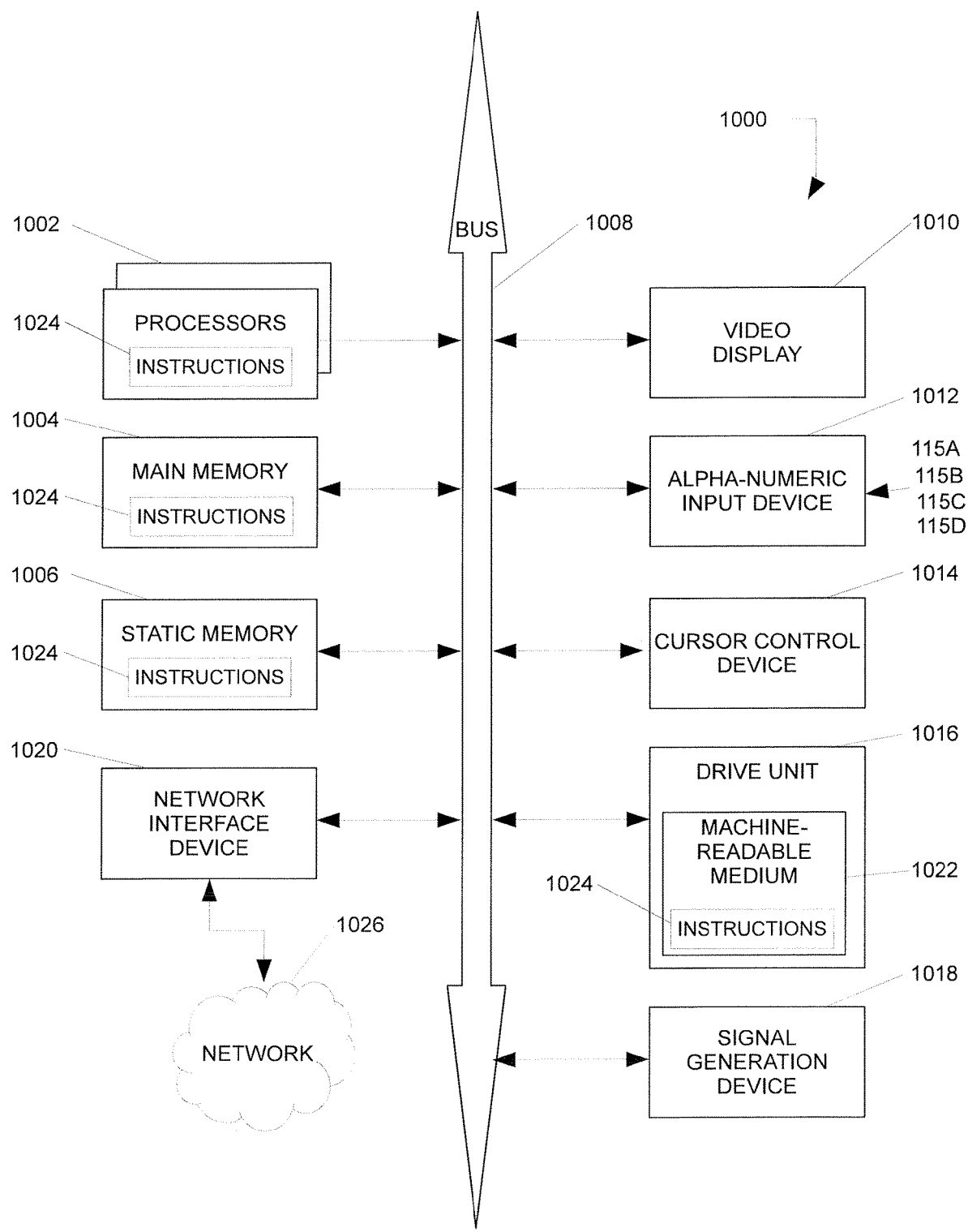
FIG. 5 is a schematic representation of a computing device for a machine in the example electronic form of a computer system, according to an example embodiment.

FIG. 5 shows a schematic representation of a computing device for a machine in the example electronic form of a Programmed logic controller computer system, within which a set of preprogramed instructions for causing the machine to perform any one or more of the methodologies discussed herein can be executed or is adapted to include the apparatus for generating operational reports as described herein. In various example embodiments, the present device operates as a standalone device is connected (e.g., networked) to other machines. In a networked deployment, this device can operate in the capacity of a client machine in a private server-client network environment. The external machine can be a personal computer (PC), a tablet PC, a set-top box (STB), a Personal Digital Assistant (PDA), a cellular telephone, a portable music player (e.g., a portable hard drive audio device such as a Moving Picture Experts Group Audio Layer 3 (MP3) player, a web appliance, a network router, a switch, a bridge, or any machine capable of executing a set of instructions (sequential or otherwise) that specify actions to be taken by that machine and the consumer of the linctus products. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes a processor or multiple processors 1002 (e.g., a central processing unit (CPU), a graphics processing unit (GPU), arithmetic logic unit or all), and a main memory 1004 and a static memory 1006, which communicate with each other via a bus 1008. The computer system 1000 can further include a video display 1010, such as video display unit 114 (e.g., a liquid crystal display (LCD) or a cathode ray tube (CRT)). The computer system 1000 also includes an alphanumeric input device 1012, such as device 115A, 115B, 115C, 115D (e.g., a keys), a disk drive unit 1016, a signal generation device 1018 (e.g., a speaker) and a network interface device 1020.

The disk drive or other drive unit includes a computer-readable medium on which is stored one or more sets of instructions 1022 and data structures (e.g., instructions) embodying or utilized by any one or more of the methodologies or functions described herein. The instructions can also reside, completely or at least partially, within the main memory and/or within the processors 1002 during execution thereof by the computer system. The main memory and the processors also constitute machine-readable media which include instruction sets 1024. The instructions can further be transmitted or received over a network 1026 via the network interface device utilizing any one of a number of well-known transfer protocols (e.g., Hyper Text Transfer Protocol (HTTP), CAN, Serial, or Modbus).

While the computer-readable medium 1022 is shown in an example embodiment to be a single medium, the term "computer-readable medium" should be taken to include a single medium or multiple media (e.g., a centralized or distributed database, and/or associated caches and servers) that store the one or more sets of instructions and provide the instructions in a computer readable form. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, tangible forms and signals that can be read or sensed by a computer. Such media can also include, random access memory (RAMs), read only memory (ROMs), and the like.

The example embodiments described herein can be implemented in an operating environment comprising computer-executable instructions (e.g., software) installed on a programmable logic controller computer, in hardware, or in a combination of software and hardware. Modules as used herein can be hardware or hardware including circuitry to execute instructions. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software programs for implementing the present method(s) can be written in any number of suitable programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Perl, UNIX Shell, Visual Basic or Visual Basic Script, Virtual Reality Markup Language (VRML), ColdFusion™ or other compilers, assemblers, interpreters or other computer languages or platforms.

Figure 6:
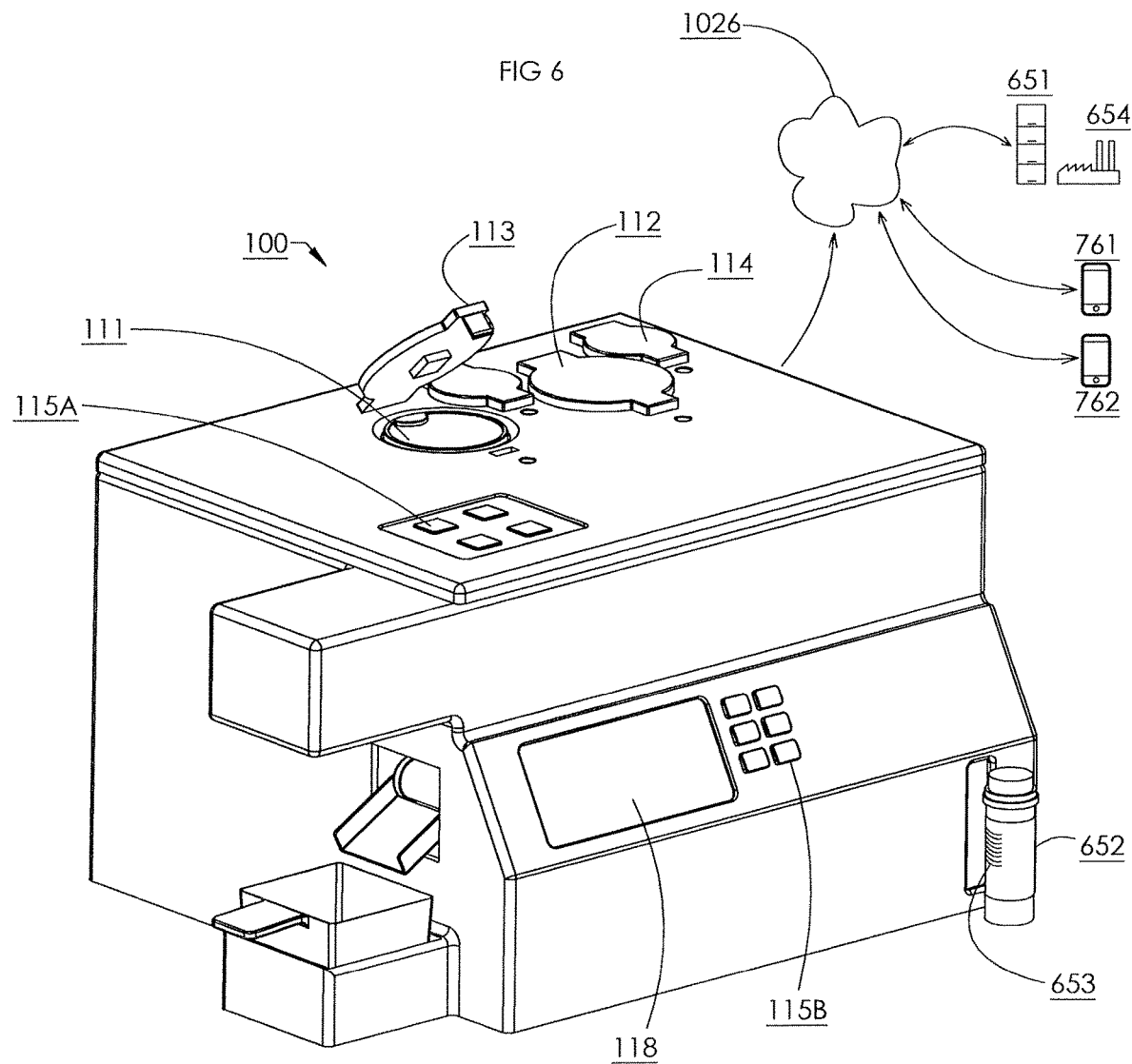
FIG. 6 is a graphic depiction of the communications enabled by the device in FIG. 1 during the filling process initiated by the user, according to an example embodiment.

FIG. 6 is a graphic depiction of the communications enabled by the device 100 in FIG. 1 during the filling process, according to an example embodiment. The filling process can be initiated by a user in one embodiment. In another embodiment, the filling process can be initiated by opening the lid 113 to one of the cylindrical containers 111 of the medication dispensary device. In one embodiment, a user enters a code or password entered at the interface, such as at buttons 115A, 115B or the screen 118 See FIG. 1). Once the lid is opened, communications could be enabled. As part of the filling process, the user could be prompted to scan a portion of a label 653 which is attached to a prescription bottle 652. A bar code or a QR code could be placed on the label 653. The bar code or QR code is encoded with information about the medication. The information could include links to various outside companies that would include information about the medication stored within the bottle 652. The information might also be a link to a pharmacy that filled the prescription. The pharmacy could have a cloud based data storage that would be available 24/7 that the medical dispensary device 100 could use to gather needed information to verify the medication. The medication dispensing apparatus 100 could communicate over a network 1026 such as the internet. The medication dispensing apparatus 100 could communicate via a hardwired connection to the internet or via WIFI. Information can be obtained from one of many sources, including but not limited to a manufacturer or a service provider 654 which retains catalog product data 651, product recommended consumption and the prescriber's product selection 650 and directions for consumption. The data can also include the size and color of the medication for a particular batch of medications.

The processor 1002 or processors include capabilities obtaining storing and referencing for linctus product data. Sensors mounted with in the device to provide physical linctus product identification such as size, shape, color, markings and weight. The physical data obtained from the manufactures product data is programmed into the processor from a variety of sources. The sources of product data may include manual input, digital input downloaded from a primary retailer network server source via VPN communications, digital input from the character recognition of the linctus product, digital images including product physical properties, radio frequency product tag, UPC barcode or QR reader on the device.

In another example embodiment, the user or operator initiates the fill process by pressing the surface mounted refill button on screen or interface 115A. The operator passing the retail linctus product container in front of the product identification code reading sensor 110 on the unit 100 begins the device fill process. These immediate operator actions eliminate the need for daily, weekly or monthly manual sorting of supplement or prescription pills or tablet into a pill container. The consumer is automatically provided the proper sorting by passing the retail prescription container past the retail container scanner. The scanner provides data stored in memory that includes specific prescription information. The specific information can also be also provided with radio, barcode, or other product identification markers. The identification data may also include the specifics of the directions to consume the prescriptions, after scanning the label of the bottle holding the medication, the user simply fills the storage cylinder by emptying the contents of the retail container into the open storage section of the designated storage cylinder 111.

The external communications are made through a wireless virtual private network connection. These communications include notifications to the consumer's home phone, cell phone, computer with voice and text messages. The communications also are made to the device retail pharmacists or other service for verification of the prescription products and dosage during the filling process. The device also communicates various monitored points in the dispensing process and reports any errant actions involved in the processes of the device.

Figure 7:
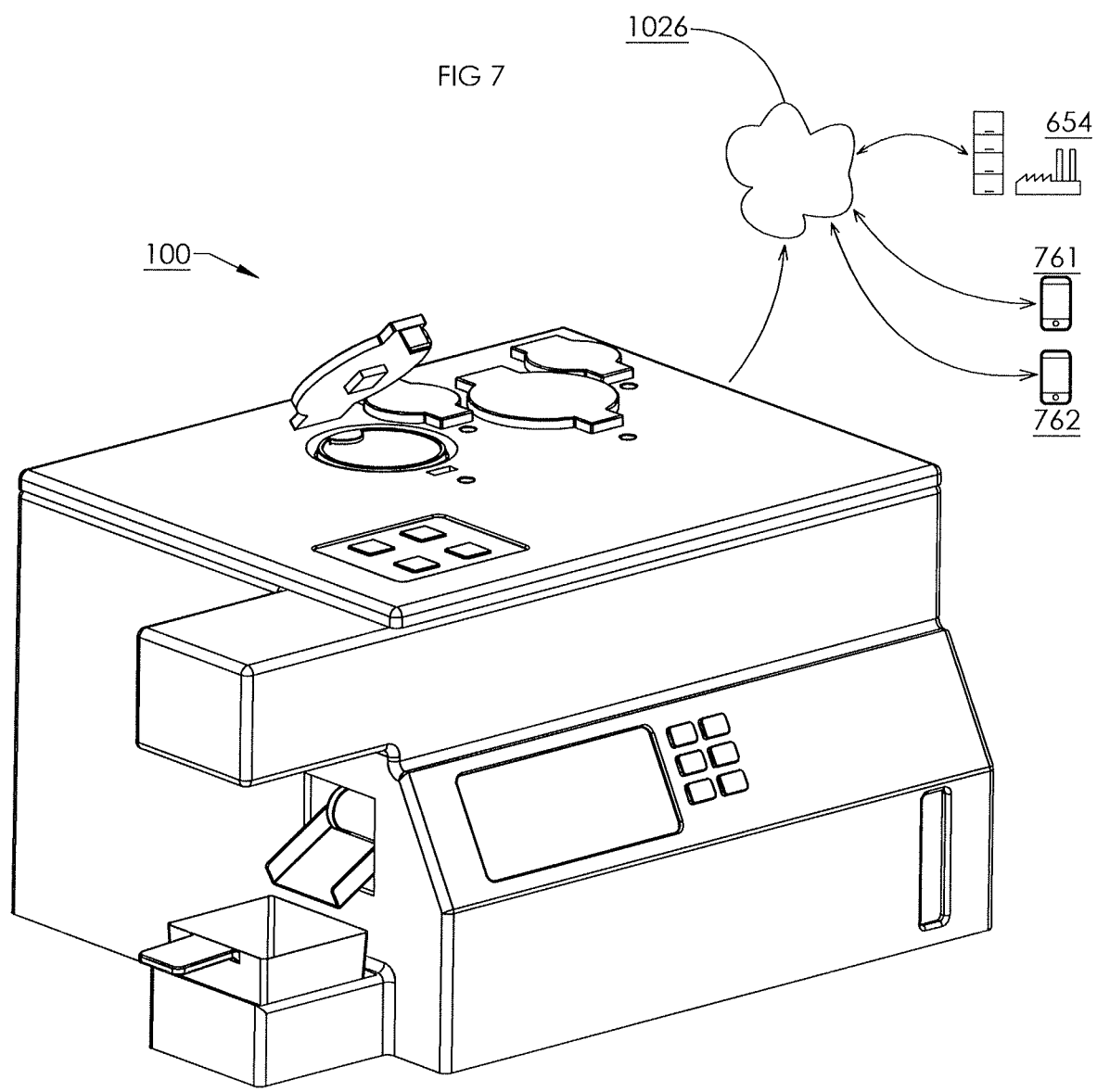
FIG. 7 is depiction showing coupling to various external devices for receiving alarms produced by an alarm processes of the medication dispensing device, according to an example embodiment.

FIG. 7 is depiction showing coupling to various external devices 761, 762, 654 for receiving alarms produced by an alarm processes of the medication dispensing device 100, according to an example embodiment. The alarm levels will generally occur at the local device 100 initially. The medical dispensing device 100 communicates to a network 1026 to various external devices. The network 1026 can be the internet, a wide area network, a local area network or the like. The network 1026 can be wireless or wired. For example, an audible or visual alarm may be enabled when a medication is dispensed by the medication dispensing device 100. The alarms are enabled at external remote devices 654, 761 and 762 after an amount of time or some other triggering event or the like. The external remote devices 654, 761, 762 are capable of receiving data. The service provider/vendor 654, in one embodiment, may be given the opportunity for real time monitoring of the device, its stores, and the operations. The remote alarm is also capable of being sent to third party devices capable of receiving data via the virtual private network digital connection, the internet, or the like. The alarms may take the form of notifications. For example, a service provider may be alerted or notified to process a refill of a certain drug when the supply within the medication dispensing device 100 reaches a low amount. The low amount can be set based on a selected threshold or can be set based on the amount of time necessary to refill a prescription. For example, the alarm or notification system could be set to give a notification or an alarm when there is 14 does left within the medical dispensing device 100. In another embodiment, the dispensing apparatus could generate an alarm based on a refill time. The time necessary to refill at the pharmacy could be 3 days. The prescription calls for the patient to take two pills per day so the machine might generate an alarm for refilling when there are 10 pills left so that there is a two day factor of safety for getting the refills done.

An alarm can also be generated when a patient does not take the medication. The alarm can be set to notify certain devices after a set amount of time. This helps with compliance or patients taking the medication prescribed. The person notified could be a home care professional or a relative. The person notified could call or otherwise contact the patient and remind them to take their medication. In some instances, the patient could be called, texted, or otherwise notified with a reminder as well.

FIG. 8 is a logic diagram for operation of certain aspects of the present invention apparatus, according to an example embodiment. FIG. 9 is a logic diagram for operation of certain aspects of the present invention apparatus, according to an example embodiment. The various flowcharts will now be discussed by referring to both FIGS. 8 and 9.

The flow charts in FIGS. 8 and 9 represent the transfer of data collected or decimated either by the present invention (local device 100) and or a central station. The central station receives encrypted data communications via a virtual private network (depicted as network 1026 in FIG. 7) from the present device. Communication is initiated by the assigned user or technicians at on the site location of the device. This initial communication remains active from that point in time forward. The external central station 1026 has 100% real time visibility of the device's components and the products to be processed by the device. The external service or central station communications interruptions are automatically re initiated by the device by way of uninterruptable or battery backup power supply with in the devices.

The central station 1026 maintains a substantially constant communications with the present device. As device performs the function of storing, sorting and delivering the individual dosage to the user, the central station receives data. Errant input from the device 100 in the course of executing the functions will be called upon by the programming of the device to create annunciated notifications classified as normal, fault or alarm. Normal activity, such as the results of properly performing the functions of the device is monitored but only for observation and record keeping. Historical data is retained as needs predict.

Security login to the local device 100 may include manual input, voice, biometric or other means of individual identification. The central operator station 1026 identifies the device, and establishes a secure connection. The central station 1026 establishes a device and user profile with data regarding the user.

This user profile include individual user personal information that relates to the processes associated with, and in conjunction with the linctus products processed, dosed, and contained in the present invention. Included in the user profile data may be identification of pharmaceuticals' retail outlet sources that the user prefers and device location and the device IP address. The names and contact information of family and friends or other interested parties or individuals such as medical, technical, doctors, consultants and other health care individuals and organizations may also be included in the user profile. Products manufacture may also find the data provided by the device as useful.

As indicated in the flow chart on FIG. 8, the fill mode of the device is initiated by the user passing the code retail container through the field of view of the devices' decoding sensors, such as sensor 110. These sensor 110 may include varying methods and forms coded identification including passive and active Radio frequency identification, ultraviolet, or ultrasound decoding, or a bar code reader or other sensor. The other sensors can be used to detect the type of linctus as well. As mentioned above, other sensors are optical and the like.

The coded data is translated from the sensing elements formatted to the local device by way of controllers and sub-processors designed specifically for the input and data form to the present invention format. The data is uploaded to the central station for verification. The coded information may include specific information about the product, directions for use and consumption as well other general or specific limitations to consumption. Other user and product data may also be encoded in the bulk container or product itself.

The product characteristics are utilized to calibrate and adjust the sorting system component s to meet the specific requirements of the product. The adjustment may include product dimensions that require a larger belt opening to facilitate a single unit be processed. The inputted data would adjust the drive mechanism program to change the belt configuration creating a larger opening in the adjustable linked belt. The weights that are required for confirmation in the storage cylinder, the tilt table and the dispensing platform are calculated and monitored based on the specific of the product.

Upon confirmation that the data from the device and the central station data match, the device opens a single storage cylinder lid, such as the lid 113 associated with storage container 111, and displays the directions to the user to empty the contents of the retail container into the open storage cylinder on the display. The directions then direct the user to close the lid of the cylinder.

The optical sensor 221A, 221B, 221C and weight sensors 222 gather data on the product with in the present invention. The controllers and sub-processors of these sensors 221A, 221B, 221C, 222 provide input in the data format required by the invention to complete product verification and handling. The specific actual details on the physical characteristics of the product color, shape, size, marking, and weight is gathered and translated to suit the device's function, utilization, confirmation and operation.

The product characteristics are utilized to calibrate and adjust the sorting system component s to meet the specific requirements of the product. The adjustment may include product dimension that require a larger belt opening to facilitate a single unit be processed. The inputted data would adjust the drive mechanism to change the belt configuration creating a larger opening in the adjustable linked belt. The weight that is required for confirmation in the storage cylinder, the tilt table FIG. 4 and the dispensing platform is calculated and monitored based on the specifics of the product.

This localized product coded information is transferred to the central station 1026 for verification. If the data does not match the recorded prescribed information on record or other source library content of product data, user and/or includes conflicting data with the limitations of another product in the device will result in an alarm condition. In this event the device generates an alarm to central station indicating the need for intervention by a technical, product or health care organization may be required.

It is presumed that the product data included will include at a minimum of information for the product such as the directions of the prescriber of the product. This information is likely to include the time the prescription was added to the device as well as the quantity. The individual dosage of the product is also saved. This data is retained at the local device and utilized to initiate the daily or regular dosage dispensing and delivery process. Any specific directions for consumption will be noted. These direction such as "take with Food" would be appear in text of the device display screen 118.

Included in FIG. 9 is the software flow diagram is depicting the flow of data for the dispensing phase 1 process. This is the portion of operation that sorts the stored bulk product from the storage cylinder, such as cylinder 111, to single dose. This action is called upon as directed by the program at a specific time of day. This is accomplished by initiating the single sort mechanical systems of locomotion to separate a single product unit from the specific storage cylinder to the tilt table FIG. 4 with in the hopper. The device weighs the single unit and passes the result onboard processor unit and memory associated with the device. The optical sensors 221A, 221B, 221C in the hopper observe, measure, and record the physical characteristic data such as color shape and marking of the product. The data from these sensors 221A, 221B, 221C is verified by the device processor 1000 (shown in FIG. 3). The process confirms the correct single unit and authorizes the process to continue to dispensary phase 2.

If the tilt table product data correctly compares to the previously recorded data on the single sorted product the tilt table then actuates dispensary phase 2 data as shown in FIG. 9. Phase 2 begins as the product is conveyed to the direction of the delivery dosage cup 116. If the product does not match the single dosage requirements the tilt table FIG. 4 rejects the product and moves the product to the sealed waste section of the invention. An alarm is sent from the local device to the central station. The central station alarm calls upon the station to take appropriate actions to resolve the errant activity.

The central station 1026 has with in the diagnostic capabilities of the present invention to observe in real time the product and the device as it performs the necessary functions. The optical sensors 221A, 221B, 221C provide a visual confirmation of the position of the product with the device. Technical assistance from the central station operators can be accomplished to resolve local issues. This action may include manual manipulation of the device components.

The final stage of the dispensary phase 2, shown in FIG. 9. is the delivery of the daily dose of the products processed and handled by this invention. The sorted single doses of products are delivered into a dosage cup 116 that will contain all of the products prescribed to consumer or patient by the physician or provider. The device will notify the consumer that the dosage is ready for consumption by way of a display, tone, vibration and/or illumination or the like, at the dispensing cup 116. The device and/or product may be fitted with certain custom sensors or receivers and transmitters that may provide data on the actual consumption of the product processed by this present device.

The notifications that the consumer receives from the device will be programmable to meet the needs of the individual. Consideration of the type and nature of the notification will include vibrations, tones illumination, language text displayed, audio messaging, and in varying degrees of intensity, volume, brilliance and tone type and the like.

The alarms associated with the present Invention may be initiated or caused by the data and/or product shown in the flow diagram of FIGS. 8 and 9. These alarms will likely be from one or more of 4 areas that relate to the device or the products processed by the device. These alarm areas include Product, Process, Patient and or the Devices components.

Product type alarms may include erroneous information present on the retail container data. This may include the wrong data as the user name or incorrect product identification on the label. The product that is filled in the device storage cylinder does not match the product specifications for the central station data library also creates and an alarm at the central station. Upon confirmation by the central station the device will take any necessary actions. The device will automatically reject the erroneous product into the sealed waste receptor 335. An alarm notification will be generated if the product that is sorted to the tilt table FIG. 4 includes more than a single unit will result. The central station in receiving an alarm and may also initiate an automated resolution process such as a reset of the sorting process.

Process and device related alarms will be a result of the device incorrectly functioning at any point in the product handling process. These alarms may also represent a point in time for regular maintenance and calibration of the device components and sensors maybe required. Events such as normal power loss will result in an alarm.

The patient or unauthorized individual may attempt to remove a product prematurely or attempt to defeat the device's security this action would result in an alarm. The response to this event may well include contact by the central station and/or an outside resource such as a doctor or drug abuse counselor Alarms may also be generated from outside resources such as the manufacture who may have a product recall or stop order from a doctor upon finding a unwanted side effect from a prescribed product processed by this invention.

The device 100 may continue to function as required if there is a loss of communication. The device 100 will try to re-establish communication until there is communication available. The central station 1026 will also be alarmed and begin the steps necessary to regain proper communications with the device 100.

The level of alarm will establish the degree of action required by the central station or the device. The level include routine, annunciation and urgent. As the device performance normal operational functions the device sends data to the central station. The time of beginning the daily functions is reported with the need to establish any action. The communications remain as required would also be considered as a routine function and reported as such.

Annunciation level of alarm is as a typical notification to the user that the product dosage is available to consumption. This would also be provided to the central station to mark the time of delivery. These types of alarms will include utilization of the display and the illumination to call attention to the product having been dispensed.

Urgent alarms may be called out to the external service or central station for catastrophic failure of the device to prevent delivery of the products as required. An attempt to defeat the security elements of the device would also result in a high level of alarm such that person contact would be initiated from central station to the device user through various means This may include communication networks or formats inside and/or outside of the device.

Other aspects of the example embodiments include initiating the fill process by pressing the surface mounted refill button 115. The operator is prompted to place the retail linctus product container in front of the product identification code reading sensor 110 on the unit 100 at the beginning of the device fill process. These immediate operator actions eliminate the need for daily, weekly or monthly manual sorting of supplement or prescription pills or tablet into a pill container. The consumer is automatically provided the proper sorting by passing the retail prescription container past the container scanner. The scanner provides data input to memory that includes specific prescription information. The specific information may be also provided with radio, barcode, or other product identification markers. The identification data may also include the specifics of the directions to consume the prescriptions. Sensor 110 initializes the product and prescription verification process by enabling digital communications with the vendor or service provider. This communication provides the device with digital information confirming the details of the specific prescription and product specific characteristics such as size, shape, color, markings and individual unit weight from the vendor or service provider product library. Once the details are confirmed, the device then releases the security latch part 26 FIGS. 2 and 3 on a specific storage container lid 113 or lids. The display 118 indicates a graphic depiction of the specific product and the details for consumption as directed by the prescription or manufacture's product consumption directions. The operator modifies or accepts the scheduled time for the linctus to be dispensed by depressing a coded button 115 on the face of the device.

When the device fill process is initiated the process causes digital communication to vendor or service provider 651. The digital data obtained upon the operator initiating the fill process includes passing the retail linctus container 52 past the present inventions sensor 10. The data contained by the coded label 653 past the code reader 110 (shown in FIG. 1) is recorded in the devices local memory. The vendor 651 communication will reference the prescriptions and product data which is recorded and retained by the device of figure one for utilization in dosage processing and dispensing. The measuring and weighing sensors verify the programmed unit data. Measures, such as shape is accomplished through OCR optical character recognition sensors verity color and shape to the program. The weight of the unit for the dispensed material is compared to the program by the weight sensors. The input may also come directly from the retailer's prescription containers which may include a digital marker with the complete details on the linctus product. The required information includes but is not limited to weight, shape, dimensions, color, marking and nomenclature. The manual input of the data may also be available.

The device mounted sensors 221A, 221B, and 221C, shown in FIG. 2, monitor the dosage, storage and dispensing of the linctus by gathering data from the physical characteristics. The process of data gathering is accomplished by the recognition of the sensors and sub processors located in the storage cylinder 111, the dosage separating section, conveying section, weight and measures section. The physical data gathered by the sensors and processors may include product weight, color, shape, size, imprinted nomenclature and weight based on data stored and obtained through the device processes and activities. The stores portion part 111 (see FIG. 2) of the base unit may include receptacles for the variable size of storage cylinders. The prescription storage receiver is a round or other shaped container which may include various dynamic and electric components that facilitate the processes associated with dispersing the tablets according to the prescribers directions. This device fully monitors the prescriptions in stored and dispensed units. The weight of the full storage cylinder 111 is continuously monitored to provide data to the digital processors to provide control and other data to the sorting, dosage and storage. When the weight gets low or the optical sensors recognizes low units in the storage cylinder indicating that the number of doses remaining are low, the device can request a refill of a prescription. The device can also monitor the number remaining in a storage bin by monitoring the number of doses which have been dispensed.

The device 100 monitors the dispensing container by weight sensors and other physical measurements of the contents on the dosage platform pad. If after an adjustable time the dispensing container has not been removed from the dosage platform pad, an audio sound or tone is generated to call attention to the invention. This tone is gradually increased to gain greater interest by the consumer to take the medications. After a period of 30 minutes (adjustable) the device auto dialer, in another example embodiment, will initiate a phone call to the home phone of the consumer with a message to take the dosage. If after another period of time the device does not have confirmation of the dosage containing being removed can send a digital text message to the consumer's cell phone or to another party that may be helping the patient.

The device 100 through the internal and external digital communications of the device monitors and verifies the status of individual materials the dosage. The data is retained in on board data storage devices. In the present invention the digital processors provide the means to record and transmit digital information to and from the inputs generated by materials in the process of the device or created by the use of the drug dispensary device. The product and manufactures data is used to program the functions and collect physical product data required to precisely dose the consumer's medications and supplement linctus.

Upon filling or refilling the storage cylinders the retail containers coded data establishes the details of the product. This retail product data is referenced and verified through the input of sensors 221, the remote microprocessors to verify the product as it moves through the storage, sorting, conveying and dispensing and the emptying the dispensing cup for the dosage consumption by the consumer. The data obtained by the product code is registered in the memory of the present device processors. This product data is verified through external communications established by the device to a third party product retailer or supplier. This communication is established via a network connection that is generated by the device to a master library or outside source for confirmation. The product receiver and storage unit of the present invention includes a cylindrical tube of varying length and diameter. The storage cylinder unit also includes a section that provides the proper dosage through mechanical or other single unit sorting process. These processes may include vibratory, sonic, or mechanical means of creating the unitary distribution of the linctus product.

The products of the prescription are contained within the storage shoe Part 111 of this device 100. The shoe includes a cradle that holds the storage cylinder that may be integral to the shoe or a replaceable container. Certain security functions are present in the device to lock and monitor the consumption of the controlled linctus materials. These may include an electromagnetic locking device or other means such as mechanical seals on the containers.

Dispensary of the linctus is provided to the consumer in the receptacle part 116 (see FIG. 1). The linctus material is then transported via a mechanical conveyor to the dosage container receiver. The receptacle is colorized by illumination. The illumination of the receptacle 116 is present during the alarm function. The tare weight of the container is sensed by weight 133 sensor in the base and observed by the optical sensor 212 mounted above the receptacle for verification of the dosage. Upon the programmed dispensing interval of the dosage the device generates an audio and visual signal notifying that the measured quantity is ready for consumption.

If the consumer is unable to reach the dosage container by being away from the device the consumer can reset the device with a digital response via text. This resolves the away from home scenario. Through various means which may include pressure or weight sensors in the shoe levels of materials in medications are monitored. This information is utilized by the processors to alert the user that it is time for refilling the device. This notification may also be transmitted to the provider and pharmacist for refill. This contact to the refill process may be local displayed on the device display screen or transmitted to the retailer for execution of the refill process.

A medication dispensing apparatus includes a housing for at storing at least one medication in bulk, a dispenser and a verification sensor. The at least one medication including a plurality of doses of the at least one medication. The dispenser separates a single dose from the at least one medication in bulk. The dispenser moves the single dose of the at least one medication from a position within the housing to a position outside the housing. The verification sensor verifies that the at least one medication is a correct medication. The verification can be done when the medication is initially input and also later on during the dispensing of the drug or medication. In one embodiment, the verification sensor matches the contents in a prescription bottle to attributes of a medication provided by a manufacturer. The medication dispensing apparatus also can include a dosage sensor that compares a single dose obtained by the dispenser to a single dose as prescribed. The medication dispensing apparatus further includes a timer that records a first time when a single dose is dispensed, and records a second time when a single does is removed from the dispenser. This can be stored and recorded. Later this can be used to produce various reports on conformance and compliance. The timers can also be used to trigger alarms and notifications. The medication dispensing apparatus includes an alarm system that produces an alarm when the time after the first time is over a threshold time. The medication dispensing apparatus, in some embodiments also includes a report generator that produces a schedule of consumption and holds the schedule of consumption in a memory. The alarm system that produces an alarm of the medication dispensing apparatus can generate an alarm, or notice or report in response to attempts to remove the at least one bulk medication from a compartment within the medication dispensing system. The medication dispensing apparatus also can include a network connection that can be used to send alarms or notifications over a network, such as the internet, to others. The others could include medical professionals, relatives and the like. In one embodiment, medication dispensing apparatus includes an RFID reader. The RFID reader reads RFIDs associated with individual doses of medication to verify the medications initially or at various stations within the device.

A medication dispensing method includes housing at least one medication in bulk, separating a single dose from the at least one medication in bulk, and moving the single dose of the at least one medication from a storage position within the housing to a dispensing position outside the housing. The at least one medication in bulk includes a plurality of doses of the at least one medication. The method also includes verifying the at least one medication in bulk as a correct medication. Verifying can include matching the at least one medication listed on a container from a pharmacy to the medication on the label. Verifying the at least one medication in bulk is a correct medication can include obtaining information about the medication from a manufacturer of the medication and visually inspecting and weighing the medication of the at least one medication in bulk. The method can also include locking the medication in bulk in a housing. In some embodiments, the medication in bulk is locked within the housing until a refill is received. The medication dispensing method can further include recording a time when a dose of the medication is dispensed and recording a time when the medication is removed from a dispensing position. The method can also include generating an alarm in response to the medication staying in the dispensing position for greater than a threshold time. The method can also include reporting on compliance of the patient, or reporting on conformance of the patient.

Certain individual's prescriptive directives for medications require that the consumption of drug be specifically monitored. The included sensor array with in the present invention may include signal receivers specifically selected for the devices to be monitored to verify consumption.

The enhanced security element in the above invention includes technology in the form of sensors and readers that provide input data on/in the consumed linctus product that may include radio frequency marker recognition data. This data may be in the form of Radio frequency that maybe measured by the invention. Advances in the linctus industry may include the creation of capsules a dissolving RF Chip printed with nontoxic electrolyte materials. The signal from that device may be recognized as it degrades thought the patient consumption. Variations of the signal are measured by this current invention to project the consumption or removal of the consumed RF device.

The devices' sensors array may also receive various forms of signals of the patient implanted, attached or carried electronic devices. This signal producing device may be providing the results of the patient having consumed the dispensed product or other vital patient information projecting the need to consume the dispensed products.

The products contained in the device are secured with multi-layer monitoring and reporting functions of the device. The above, in summary, discloses:
 a. a method to measure and record data related to the consumption of a medications;
 b. a method to provide a marker and notification of a point in time for consumption of medications;
 c. a method to record accuracy of the consumption schedule;
 d. a method of reminder for consumer include specific actions on/with the consumption of medications;
 e. a method of real time stationary communications between the linctus consumer and with a network of individuals that may include technical, health, treatment, consultants, aid, devices and pharmaceutical distribution systems and personnel;
 f. a method of receiving, storing and retrieving data regarding or specifically to an the individual's consumption of medications, need to consume medications and other patient data gathered and transferred from a patient implanted, or patient carried monitoring devices;
 g. a method of assuring that the contents in the retail container matches the specifics of the prescriptions as directed by the health care provider;
 h. a secure method to limit and restrict access to harmful or addictive medications by non-authorized persons;
 i. a method to alarm and notify that prescriptions and medications are in jeopardy of being misused by an unauthorized person;
 j. a platform to communicate ones real time health status to an interested third party;
 k. a method to fulfill the elements of compliance and conformance standards and industry recommendations to accurately control proper dosages of consumer pharmaceuticals and supplements;
 l. a method to secure an individual prescribed drugs; and
 m. a method to sort and deliver bulk retail container drugs into single dose, and the like.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. It will be apparent to one of ordinary skill in the art that many modifications and variations are possible in view of the above teachings.

The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

While the embodiments have been described in terms of several particular embodiments, there are alterations, permutations, and equivalents, which fall within the scope of these general concepts. It should also be noted that there are many alternative ways of implementing the methods and apparatuses of the present embodiments. It is therefore intended that the following appended claims be interpreted as including all such alterations, permutations, and equivalents as fall within the true spirit and scope of the described embodiments.

What is claimed:

1. A medication dispensing method comprising:
 housing at least two medications in bulk from a pharmacy container, the housing further comprising:
 a first lockable container for securing a first medication in bulk; and
 a second lockable container for securing a second medication in bulk;
 the at least two medications in bulk including a plurality of single daily doses of the medication in bulk;
 separating a single daily dose of the first medication from the first lockable container,
 separating a single daily dose of the second medication from the second lockable container;

moving the single daily dose of the first medication from the first lockable container within the housing to a dispensing position outside the housing; and moving the single daily dose of the second medication from the second lockable container within the housing to a dispensing position outside the housing, the dispensing position being an open cup outside the housing;

comparing optical data for the single daily doses of the first medication and the single daily dose of the second medication to manufacturers data for a first prescription for the first medication, and to manufacturers data for a second prescription for the second medication;

comparing an actual weight of a single individual daily dose obtained by a scale of the first medication to a manufactured weight of a single daily dose of a prescribed medication;

redirecting the single daily dose of a first medication that does not match data for a single dose of that medication to an errant medication receptacle; and redirecting the single daily dose of a second medication that does not match data for a single dose of that medication to an errant medication receptacle.

2. The medication dispensing method of claim 1 further comprising verifying the at least one medication in bulk is a correct medication.

3. The medication dispensing method of claim 1 further comprising verifying the at least one a single daily dose of at least one of the first medication and the second medication matches a prescription from a pharmacy.

4. The medication dispensing method of claim 1 further comprising verifying the at least one medication in bulk is a correct medication by obtaining information about the medication from a manufacturer of the medication and visually inspecting and weighing a single daily dose of the at least one medication in bulk.

5. The medication dispensing method of claim 1 further comprising locking the first lockable container in the housing until the first medication in the first lockable container has been dispensed.

6. The medication dispensing method of claim 1 further comprising locking the first lockable container until a refill of the first medication is received.

7. The medication dispensing method of claim 1 further comprising recording a time when a single daily dose of the first medication is dispensed and recording a time when the single daily dose of the first medication is removed from the open cup at the dispensing position.

8. The medication dispensing method of claim 7 further comprising generating an alarm in response to the first medication staying in the dispensing position for greater than a threshold time.

9. The medication dispensing method of claim 1 further comprising reporting on compliance of the patient.

10. The medication dispensing method of claim 1 further comprising reporting on conformance of the patient.

11. The medication dispensing method of claim 1 wherein comparing optical data for the single daily doses of the first medication and the single daily dose of the second medication to manufacturers data for a first prescription for the first medication, and to manufacturers data for a second prescription for the second medication includes:

comparing the shape and size of the first prescription for the first medication to the manufactures data on shape and size; and comparing the shape and size of the second prescription for the second medication to the manufactures data on shape and size.

12. A personal individual daily medication dosage dispensing apparatus comprising:

a housing including a first lockable container within the housing to securely hold a first daily dosage medication in bulk, the first daily dosage medication including a plurality of single individual daily doses of the first medication; and a second lockable container within the housing to securely hold a second daily dosage medication in bulk, the second daily dosage medication including a plurality of second individual daily doses of the second medication;

a dispenser for separating a single individual daily dose of the first medication from the first daily dosage medication in bulk, the dispenser also separating a single individual daily dose of the second medication from the second daily dosage medication in bulk;

a conveyor for moving the single individual daily dose of the first medication and for moving the single individual daily dose of the second medication from a position within the housing to an output tray including a portion outside the housing; and an optical pill verification sensor for verifying the single individual daily dose of the first medication is a correct medication, and for verifying that the single individual daily dose of the second medication is a correct medication, the optical pill verification sensor located between the output tray and the first and second lockable containers, the optical pill verification sensor further comprising a scale that compares an actual weight of a single individual daily dose obtained by the dispenser to a manufactured weight of a single daily dose of a prescribed medication, the medication dispensing apparatus optical dosage verification sensor compares visual attributes of a single individual daily dose obtained by the medication dispensing apparatus to visual attributes of a single daily dose of the prescribed medication; and an errant dosage receptacle for an unverified single individual daily dose of the first medication or the second medication.

13. The medication dispensing apparatus of claim 12 wherein the optical pill verification sensor matches a first prescription to attributes of a the single individual daily dose of the first medication provided by a manufacturer of the first medication, and matches a second prescription to attributes of the single individual daily dose of the second medication provided by a manufacturer of the second medication.

14. The medication dispensing apparatus of claim 12 further including a dosage cup sensor for gathering data including a first dispense time for the first medication and the second medication and quantity of the first single individual daily dose and the quantity of the second individual daily dose as dispensed.

15. The medication dispensing apparatus of claim 14 wherein the dosage cup sensor records a second time when the first single individual daily dose and the second single individual daily dose is removed from the output tray.

16. The medication dispensing apparatus of claim 15 further comprising an alarm system that produces an alarm when the time after the difference between the second time and the first time is over a threshold time.

17. The medication dispensing apparatus of claim 15 further comprising a report generator that produces a schedule of consumption and holds the schedule of consumption in a memory.

18. The medication dispensing apparatus of claim 12 further comprising an alarm system that produces an alarm in response to attempts to remove the at least one bulk medication from a compartment within the medication dispensing system.

19. The medication dispensing apparatus of claim 12 further comprising a network connection.

20. The medication dispensing apparatus of claim 12 wherein the verification system included an RFID reader, the RFID reader reading RFIDs associated with individual doses of medication.

21. The medication dispensing apparatus of claim 12 wherein the verification system included bar code scanner for scanning bar codes associated with individual doses of medication.

22. The medication dispensing apparatus of claim 21 wherein the bar code scanner can scan UPC codes associated with individual doses of medication.

23. The medication dispensing apparatus of claim 2 wherein the verification system included QR code scanner for scanning QR codes associated with individual doses of medication.

24. The medication dispensing apparatus of claim 2 wherein the verification system included QR code scanner for scanning QR codes associated with individual doses of medication.

* * * * *